United States Patent [19]

Blain et al.

[11] Patent Number: 4,994,197

[45] Date of Patent: Feb. 19, 1991

[54] TRIAZOLE COMPOSITIONS AS FUEL AND LUBE ADDITIVES

[75] Inventors: David A. Blain, Mount Laurel; Angeline B. Cardis, Florence, both of N.J.

[73] Assignee: Mobil Oil Corporation, New York, N.Y.

[21] Appl. No.: 452,073

[22] Filed: Dec. 18, 1989

[51] Int. Cl.$^5$ ............... C10M 133/44; C10M 135/58; C10L 1/22
[52] U.S. Cl. ................................. 252/51.5 A; 44/336; 548/261
[58] Field of Search ................. 252/51.5 A; 548/261; 44/63

[56] References Cited

U.S. PATENT DOCUMENTS

| | | | |
|---|---|---|---|
| 3,518,193 | 6/1970 | Cyba | 252/49.6 |
| 3,573,205 | 3/1971 | Lowe et al. | 252/51.5 A |
| 3,844,965 | 10/1974 | Brown | 252/51.5 A |
| 4,113,725 | 9/1978 | Nmadi et al. | 252/47.5 |
| 4,116,875 | 9/1978 | Nmadi et al. | 252/49.7 |
| 4,235,730 | 11/1980 | Schlicht | 252/51.5 A |
| 4,238,296 | 8/1981 | Nebzydoski et al. | 252/49.9 |
| 4,464,276 | 8/1984 | Sung et al. | 252/42.7 |
| 4,713,191 | 12/1987 | Nalesnik | 252/51.5 A |
| 4,855,074 | 8/1989 | Papas | 252/51.5 A |

Primary Examiner—Olik Chaudhuri
Assistant Examiner—Jerry D. Johnson
Attorney, Agent, or Firm—Andrew J. McKillop; Charles J. Speciale; L. G. Wise

[57] ABSTRACT

Triazole compounds are grafted onto alkyl or alkenyl succinimides by using diisocyanates to effect the coupling. The process is carried out by first reacting a 1,2,3-triazole with a diisocyanate to produce a triazole substituted urea addition product containing a single unreacted isocyanato group. This intermediate reaction product is then reacted with an alkyl or alkenyl succinimide ashless dispersant prepared from an alkyl or alkenyl succinic acid or anhydride and a polyamine by known methods. The novel composition so produced comprises a multifunctional hydrocarbon fuel or lubricant additive.

24 Claims, 1 Drawing Sheet

TRIAZOLE COMPOSITIONS AS FUEL AND LUBE ADDITIVES

This invention relates to novel fuel and lubricant additives, methods for their preparation and to fuel and lubricant mixtures containing these additives More particularly, the invention relates to additives prepared by grafting triazoles onto alkyl or alkenyl succinimides derived from reaction between polyalkylene amines and substituted succinic anhydrides These additives are useful, inter alia, as antioxidants, dispersants, corrosion inhibitors and antiwear agents.

BACKGROUND OF THE INVENTION

The formulation of hydrocarbon and oxygen containing fuels and lubricants typically includes additives comprising a variety of chemicals to improve properties in application specific situations, particularly gasoline and diesel internal combustion engines. The more commonly used additives include oxidation inhibitors, rust inhibitors, metal passivators, antiwear agents, extreme pressure additives, pour point depressants, detergent-dispersants, lube viscosity index (VI) improvers, foam inhibitors and the like. The scope of the operating conditions to which internal combustion engines are subjected can readily result in lubricant degradation, leading to sludge buildup and excessive engine wear. The foregoing additives serve to control this problem in various ways. In the lubricant arts, this aspect is specifically described in Kirk-Othmer "Encyclopedia of Chemical Technology", 3rd edition, Vol. 14, pp 477-526, incorporated herein by reference.

It is known that alkenyl succinimides prepared from alkenyl succinic anhydrides and polyalkyleneamines are effective as additives to provide ashless dispersancy. These are typically prepared from materials such as polyisobutenyl succinic anhydride and tetraethylene penatamine. Examples of such succinimides are described in U.S. Pat. Nos. 3,024,237, 3,172,892, 3,202,678, 3,219,666 and 3,257,554. It is also known that further derivation of alkenyl succinimides can be accomplished to enhance the dispersant properties of these succinimides or to augment these properties with additional functions, such as improved antioxidant properties and the like.

In U.S. Pat. No. 3,573,205, Lowe suggests the reaction product of alkenyl succinimide and diisocyanate as a lubricant additive. Brown, in U.S. Pat. No. 3,844,965, discloses the reaction product of a hydrocarbyl susituted cyclic imide lube oil ashless dispersant with an organic polyisocyanate and a polyoxyalkylene polyol as an antirust additive.

In U.S. Pat. No. 4,713,191 to Nalesnik it is disclosed that lubricant additives can be prepared from coupling alkenyl succinimides using hydroxycarboxylic acids and diisocyanates.

The U.S. Pat. No. 4,116,875 to Nmadi et al discloses lubricant additives comprising bis-alkenyl succinimides coupled by hetercyclic compounds. The heterocyclic compounds include triazenes. The triazene may be further reacted, in one embodiment, to produce a lactam amino group. Further, in U.S. Pat. No. 4,113,725, Nmadi et al provides structures for lubricant additives employing hetercyclic nitrogen compounds including triazenes, plus alkenyl succinimides.

In U.S. Pat. No. 4,464,276, Sung et al discloses benzotriazole complexes with polyoxyalkylene polyamines. The patent discloses the use of alkenly succinimide/-polyamines with the products of the invention as lubricant additives.

Nebzydoski et al, in U.S. Pat. No. 4,283,296, discloses triazole based lubricating oil additives where the triazole moiety is incorporated into succinamic acid by C substitution on the triazole ring. The patentee employed, 3-amino-1, 2, 4-triazole as reactant with alkyl substituted succinic anhydride to produce and claim an amine salt as the reaction product.

Fused ring triazoles, such as benzotriazole, are known to exhibit metal passivating or anti-corrosive properties, particularly with copper based metals. They are, as well, potentially useful as antioxidants. Accordingly, the present invention is concerned with the incorporation of triazoles into molecular structures known to exhibit useful additive properties, such as alkenyl succinimides, to provide improved additives offering a multifunctional dimension as additives for fuels or lubricants. While the foregoing cited prior art describes triazole based lube additives and also the diisocyanate coupling of alkenyl succinimides, the prior art does not teach the method or compositions of the present invention wherein triazoles are coupled with alkenyl succinimides using diisocyanates.

It is an object of the present invention to provide novel, multifunctional fuel and lubricant additives incorporating triazole moieties and alkenyl succinimides.

It is another object of the instant invention to provide a method for producing the foregoing novel, multifunctional additives for mineral oil or synthetic lubricants.

Another object of the invention is to provide novel fuel and lubricant compositions incorporating the additives of the present invention.

SUMMARY OF THE INVENTION

In the present invention it has been established that triazole compounds can be grafted onto alkyl or alkenyl succinimides by using diisocyanates to effect the coupling. The process is carried out by first reacting a 1,2,3-triazole with a diisocyanate in a manner so as to produce a triazole substituted urea addition product containing a single unreacted isocyanato group. This intermediate reaction product is then reacted with an alkyl or alkenyl succinimide ashless dispersant prepared from an alkyl or alkenyl succinic acid or anhydride and a polyamine by known methods. The novel composition so produced comprises a multifunctional hydrocarbon fuel or lubricant additive that exhibits antioxidant activity by virtue of the added triazole moiety while retaining ashless dispersant qualities through the function of the succinimide moiety.

The 1,2,3-triazoles used in the present invention are preferably aromatic hydrocarbon fused ring triazoles such as benzotriazole and tolyltriazole. However substituents on the aromatic hydrocarbon ring include $C_1$-$C_{12}$ alkyl groups.

The alkyl or alkenyl succinimides are prepared from suitably substituted succinic acids or anhydrides where the alkyl or alkenyl moiety contains from 8 to 10,000 carbon atoms and is preferably polyisobutenyl. The polyamine reactant includes polyalkyleneamines having the formulae $H_2N(C_mH_{2m}NH)_{x'}H$ where m is an integer of from 2 to 12 and $x'$ is an integer preferably from 2 to 10.

Useful diisocyanates for the present invention include tolylene diisocyanate, or 4-methyl-1,3-phenylene diisocyanate, trimethylhexamethylene diisocyanate and 1,6-hexamethylene diisocyanate.

arylalkyl, or alkylaryl group. The triazole and diisocyanate can be reacted in 1:1 to 2:1 ratio.

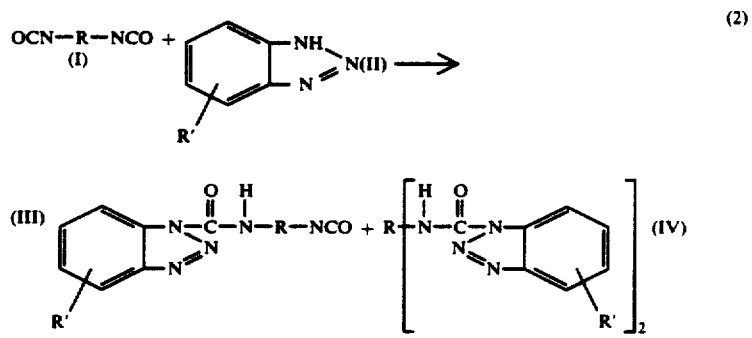

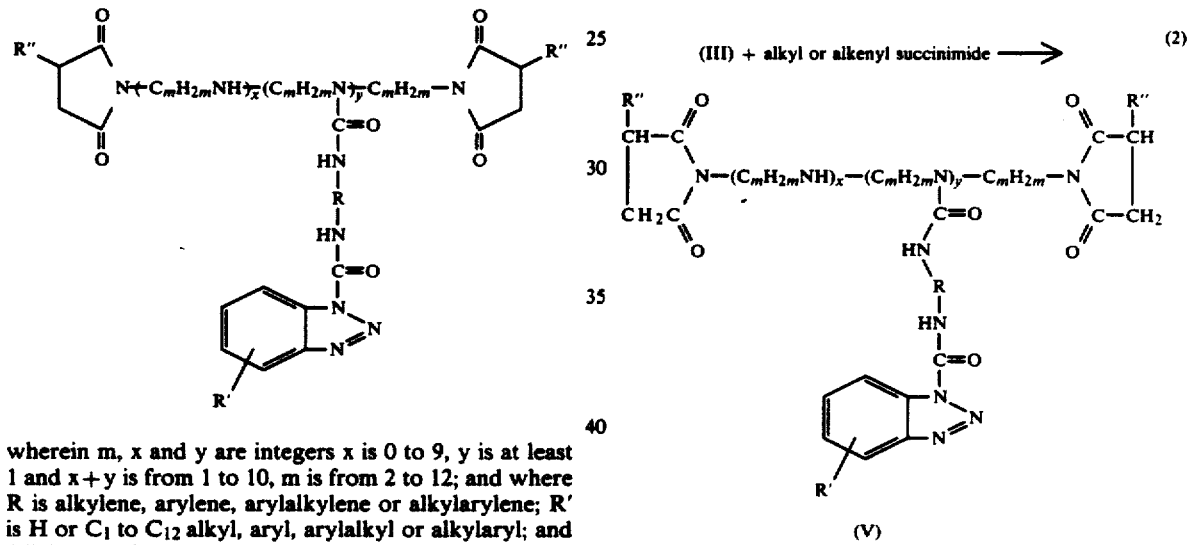

More particularly, a fluid lubricant or fuel additive composition is disclosed containing an amount sufficient of a compound of the following structure to provide anti-oxidant, antiwear or detergent properties thereto:

wherein m, x and y are integers x is 0 to 9, y is at least 1 and x+y is from 1 to 10, m is from 2 to 12; and where R is alkylene, arylene, arylalkylene or alkylarylene; R' is H or $C_1$ to $C_{12}$ alkyl, aryl, arylalkyl or alkylaryl; and R" is an alkenyl group containing from 8 to about 10,000 carbon atoms.

The invention further discloses a liquid lubricant or fuel composition comprising a major portion of an organic fluid lubricant or fuel medium and a minor portion of an additive of the above structure in an amount sufficient to provide detergent, anti-oxidant or antiwear properties thereto.

DETAIL DESCRIPTION OF THE INVENTION

Figure 1:
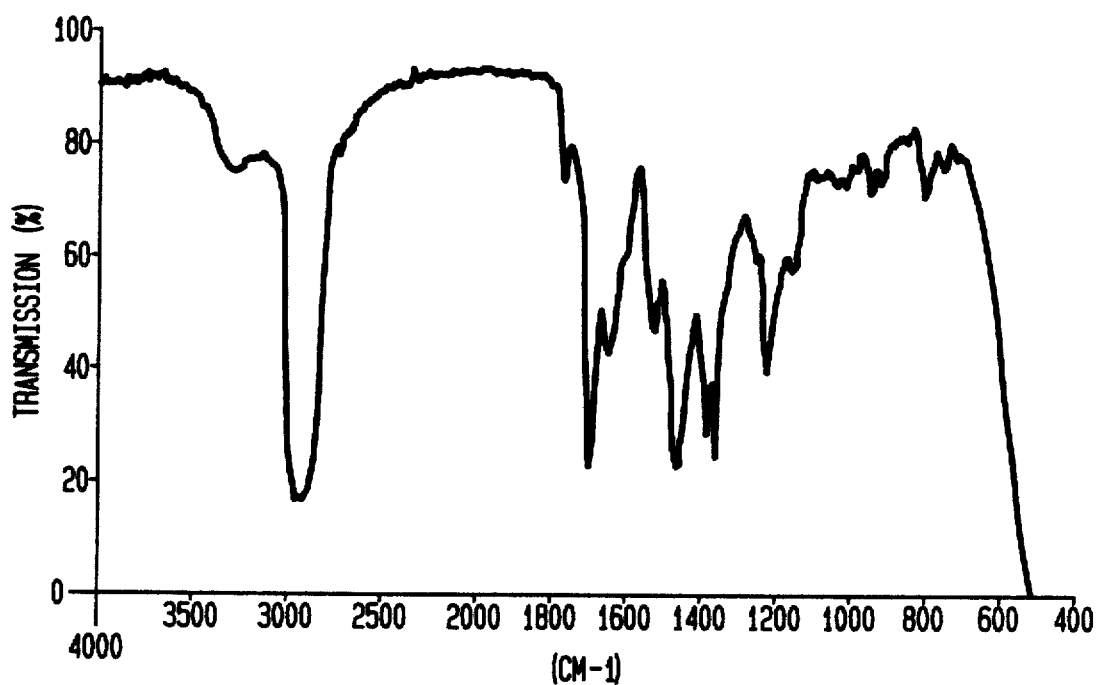
FIG. 1 is the infrared spectrum of the reaction product from Example 1 of the present invention.

Triazoles, in the instant invention, are attached to alkyl or alkenyl succinimides using diisocyanates to give a structure represented by, but not limited to, the structure represented below as (V). (I) through (V) illustrates the overall reaction sequence for the invention. In the first step (1), a diisocyanate, where R is alkylene, arylene, arylalkylene, or alkarylene, is reacted with a trizaole in which R' = H or a $C_1$ to $C_{12}$ alkyl, aryl, In Step (2) the monoisocyanato triazole (III) is reacted with an alkyl or alkenyl succinimide to produce (V).

(III) + alkyl or alkenyl succinimide ⟶ (2)

wherein m, x and y are integers x is 0 to 9, y is at least 1 and x+y is from 1 to 10, m is from 2 to 12; and where R is alkylene, arylene, arylalkylene or alkylarylene; R' is H or $C_1$ to $C_{12}$ alkyl, aryl, arylalkyl or alkylaryl; and R" is an alkenyl group containing from 8 to about 10,000 carbon atoms.

The product (III) of the first step of the reaction is preferably reacted in a 1:1 to x+y:1 ratio with an alkyl or alkenyl substituted succinimide where R" is from 8 to about 10,000 carbon atoms, preferably a $C_9$ to $C_{150}$ alkyl group, particularly polyisobutylene, and x+y=1 to 10 with y>0.

The polyamine alkyl or alkenyl succinimides used to prepare the additives of the instant invention are obtained by reacting various polyamines with an alkenyl or alkyl succinic anhydride wherein the alkenyl group is derived from a polymer of a monoolefin containing 2 to 12 carbon atoms. Preferably the monoolefin is isobutene and the alkenyl group contains from 8 to 10,000 carbon atoms. Typically, the alkenyl succinic anhydride is reacted with the polyamine in a molar ratio of 2 to 1. The succinimides employed in the present invention have the structure

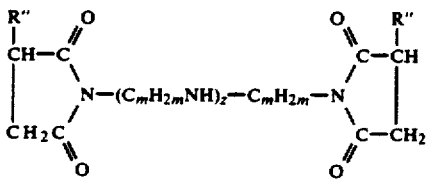

where z is an integer of from 1 to 9, m is an integer of from 2 to 12 and R" is an alkenyl group containing from 8 to about 10,000 carbon atoms.

The reaction of a polyamine with alkenyl or alkyl succinic anhydride to produce the polyamino alkenyl or alkyl succinimides employed in the present invention is well known in the art and is disclosed in U.S. Pat. Nos. 2,992,708; 3,018,291; 3,024,237; 3,100,673; 3,219,666; 3,172,892, and 3,272,746. The above are incorporated herein by reference for their disclosures of preparing alkenyl or alkyl succinimides.

The preparation of the alkenyl-substituted succinic anhydride by reaction with a polyolefin and maleic anhydride has been described, e.g., U.S. Pat. Nos. 3,018,250 and 3,024,195. The methods include the thermal reaction of the polyolefin with maleic anhydride. Reduction of the alkenyl-substitution succinic anhydride yields the corresponding alkyl derivative.

The polyolefin polymers for reaction with the maleic anhydride are polymers comprising a major amount of $C_2$ to $C_5$ mono-olefin, e.g., ethylene, propylene, butylene, isobutylene and pentene. The polymers can be homopolymers such as polyisobutylene as well as copolymers of 2 or more such olefins. The polyolefin polymer usually contains from about 8 to 10,000 carbon atoms, although preferably 20 to 300 carbon atoms. A preferred class of olefin polymers comprises the polybutenes, which are prepared by polymerization of one or more of 1-butene, 2-butene. Polymers of isobutene are particularly preferred. Usually, isobutene units constitute at least 80% of the units in the polymer. Methods for the preparation of these materials are found in U.S. Pat. Nos. 3,215,707; 3,231,587; 3,515,669; and 3,579,450, as well as U.S. Pat. No. 3,912,764.

Polyamines, or polyalkyleneamines, used to prepare the foregoing succinamides have the formula $H_2N-(C_mH_{2m}NH)_{x'}-H$, where m is from 2 to 12 and x' is from 2 to 10. Prefered polyamines include the ethylene polyamine (m=2), x' is 2 (diethylenetriamine), x is 3 (triethylenetetramine), x' is 4 (tetraethylenepentamine) and the like. Polyalkylenepolyamines such as diethylenetriamine have at least one reactive internal secondary amine group and terminal primary amine groups.

The polyamine employed to prepare the polyamino alkenyl or alkyl succinimides used in the process of this invention is preferably a polyamine having from 2 to about 12 amine nitrogen atoms. The polyamine is reacted with an alkenyl or alkyl succinic anhydride to produce the polyamino alkenyl or alkyl succinimide, employed in this invention. The polyamine is so selected so as to provide at least one basic amine per succinimide.

In many instances the polyamine used as a reactant in the production of succinimides of the present invention is not a single compound but a mixture in which one or several compounds. For example, tetraethylene pentamine prepared by the polymerization of aziridine will have both lower and higher amine member, e.g., triethylene tetramine, substituted piperaimes and pentaethylene hexamine, but the composition will be largely tetraethylene pentamine and the empirical formula of the total amine composition will closely approximate that of tetraethylene pentamine. Methods of preparation of polyamines and their reactions are detailed in Sidgewick's "The Organic Chemistry of Nitrogen" Clarendon Press, Oxford, 1966; Noller's "Chemistry of Organic Compounds", Saunders, Philadelphia, 2nd Ed., 1957; and Kirk-Othmer's "Encyclopedia of Chemical Technology", 2nd Ed., especially Volumes 2, pp. 99-116.

Triazoles effective in the present invention include all 1,2,3-triazoles and, preferably, aromatic triazoles such as benzotriazole, tolyl triazole and other benzotriazole derivatives containing substituents on the benzene ring, including $C_1-C_{12}$ alkyl, aryl, arylalkyl, or alkylaryl groups.

Aromatic and aliphatic diisocyanates are useful in the present invention; in particular, tolylene 2,4 and 2,6-diisocyanate, trimethylhexamethylene diisocyanate, hexamethylene diisocyanate and the like. Such diisocyanates have the formula OCN—R—NCO, where R is alkylene, arylene, arylalklyene, or alkylarylene.

In the process of the present invention, preferably equimolar quantities of triazole and diisocyanate are reacted to produce the monoisocyanoto triazole derivative (III). However, the reaction may also be caried out in an excess of triazole. Some formation of the symetrical substituted urea (IV) occurs as well from the reaction of two molecules of triazole with one of diisocyanate. Generally, the reaction is carried out in solution, but may also be carried out without solvent. Reaction temperatures can be from −20° C. to 250° C. Preferably, the process is carried out in an inert solvent such as xylene or other aromatic or aliphatic hydrocarbon at a temperature between 20° C. and 100° C.

After formation of the monoisocyanato triazole, the reaction mixture, or the isolated monoisocyanoto triazole, is added to the alkenyl succinimide to produce the addition product (V) of the present invention. This reaction, preferably, is carried out in inert hydrocarbon solvent at temperatures between −20° C. and 250° C.

In the overall process of this invention the molar ratio of triazole to diisocyanate to alkenyl succinimide is preferably between about 1:1:1 to 10:10:1. Depending upon the available amino groups on the succinimide and on the reactant ratios selected, the product of the invention (V) will contain from 1 to 10 triazole groups by addition of the isocyanato triazole. The foregoing available amino groups are, themselves, determined by the selection of the polyamine used to reaction with alkenyl succinimide to prepare the succinimide.

The following examples serve to illustrate the process of this invention.

EXAMPLE 1

Step 1: Tolyltriazole (6.6 g, 0.05 mole) and 75 ml xylenes is charged to a 250 ml 4-neck flask equipped with an overhead stirrer, thermometer, condenser, and addition funnel containing tolylene diisocyanate (8.7 g, 0.05 mole) in 50 ml xylenes. The reaction is heated. The tolytrizaole goes into solution at about 68° C. at which point the tolylene diisocyanate/xylenes solution is added dropwise over 30 minutes. The reaction mixture is then refluxed for two hours.

Step 2: A polyisobutenyl succinimide (146 g, 0.05 mole, made by reacting 920 MW polyisobutylene and maleic anhydride, followed by one half equivalent of tetraethylene pentamine) and 100 ml toluene are charged to a 500 ml 4-neck flask equipped with a thermometer, overhead stirrer, and heated addition funnel. The hot reaction mixture from Step 1 is transferred to the addition funnel and it is added dropwise over 30 minutes. After an additional 15 minutes of stirring an infrared spectrum of the reaction mixture shows no isocyanate peak (ca 2300 cm$^{-1}$). The reaction is stripped via rotary evaporation and filtered through a pad of heated celite filter aid.

EXAMPLE 2

The procedure from Example 1 is followed with the following exception: The ratio of tolytrizaole to diisocyanate to polyisobutenyl succinimide is changed from 1:1:1 to 2:2:1.

EXAMPLE 3

The procedure from Example 1 is followed with the following exception: The ratio of tolytriazole to diisocyanate to polyisobutenyl succinimide is changed from 1:1:1 to 2:1:1.

EXAMPLE 4

The procedure from Example 1 was followed with the following exception: Trimethylhexamethylene diisocyanate was used in place of tolylene diisocyanate.

By measuring change in viscosity, the following example shows the antioxidant capabilities of these multifunctional lubricant additives at a 4% level in a fully formulated marine diesel lubricant. The B-10 catalytic oxidation test is described in U.S. Pat. No. 4,715,974 which is incorporated herein by reference for details of the test procedure.

EXAMPLE 5

B-10 Catalytic Oxidation Test

375° F., 24 Hours

| Additive | % Δ KV |
| --- | --- |
| None | 113 |
| Example 1 | 85 |
| Example 2 | 80 |
| Example 3 | 71 |
| Example 4 | 92 |

The following example also shows the antioxidant capabilities of these multifunctional lubricant additives at 1% level in a solvent paraffinic neutral base oil.

EXAMPLE 6

B-10 Catalytic Oxidation Test

325° F., 40 Hours

| Additive | % Δ KV |
| --- | --- |
| None | 164. |
| Example 2 | 147 |
| Example 3 | 88.4 |

Both Examples 5 and 6 clearly show the effectiveness of the products of this invention in reducing the oxidative degradation of the lubricant under test conditions.

The products of this invention can be added to a fuel by mixing the products of the invention at about 25 lbs to about 500 lbs of additive per 1000 barrels of fuel. It can be added to a lubricant by mixing at about 0.1% to 10% by weight.

Figure 2:
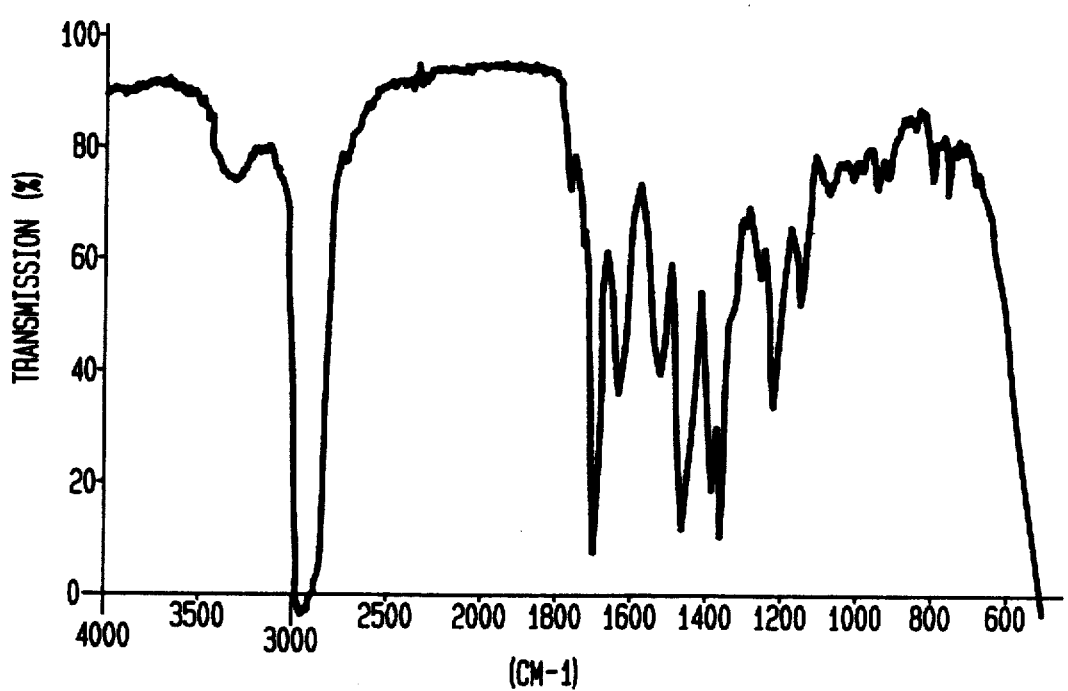
FIG. 2 is the infrared spectrum of the reaction product from Example 4 of the present invention.

In FIGS. 1 and 2 the infrared spectrum is shown for the reaction products from Examples 1 and 4, respectively. The spectrum was determined on the neat reaction product from Examples 1 and 4 of the invention and corresponds to a comprehensive characterization of those products.

While the invention has been described by specific examples and embodiments, there is no intent to limit the inventive concept except as set forth in the following claims.

What is claimed is:

1. A fluid lubricant additive composition containing a compound of the following structure:

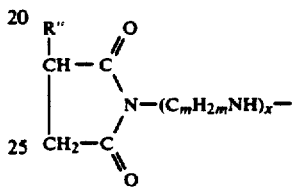

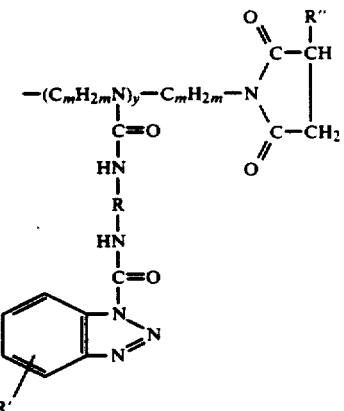

wherein m, x and y are integers x is 0 to 9, y is at least 1 and x+y is from 1 to 10, m is from 2 to 12; and where R is alkylene, arylene, arylalkylene or alkylarylene; R' is H or $C_1$ to $C_{12}$ alkyl, aryl, arylalkyl or alkylaryl; and R" is an alkenyl group containing from 8 to about 10,000 carbon atoms.

2. The composition of claim 1 wherein R is tolylene, x+y is 3 and m is 2.

3. The composition of claim 1 wherein R is hexamethylene and x+y is 3.

4. The composition of claim 1 where R" is polyisobutenyl.

5. The composition of claim 1 where R' is methyl.

6. The composition according to claim 1 further containing a compound of the following structure:

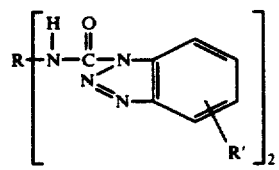

wherein R is alkylene, arylene, arylalkylene or alkylarylene and R' is H or $C_1$ to $C_{12}$ alkyl, aryl, arylalkyl or alkylaryl.

7. The composition of claim 6 wherein the variables R in each of the compounds are tolylene or hexamethylene and the variables R' in each of the compounds are methyl or hydrogen.

8. A liquid lubricant additive composition comprising the reaction product between:
(a) the monoisocyanato reaction product from the reaction of a diisocyanate compound and a 1,2,3-triazole; and
(b) the succinimide reaction product from the reaction of an alkenyl or alkyl succinic acid, or derivative thereof, and a polyalkylenepolyamine having at least one internal secondary amine group and terminal primary amine groups; wherein the ratio of said triazole to diisocyanate to said succinimide is between 1:1:1 and 10:10:1.

9. The composition of claim 8 wherein said diisocyanate includes alkylene or arylene diisocyanate and said triazole has the structure

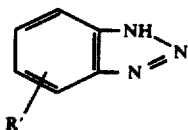

where R' is H or $C_1$ to $C_{12}$ alkyl, aryl, arylalkyl or alkylaryl.

10. The composition of claim 9 wherein said diisocyanate includes tolylene and hexamethylene diisocyanate, and said triazole includes benzotriazole and tolylenyl-triazole.

11. The composition of claim 8 wherein said succinimide has the structure

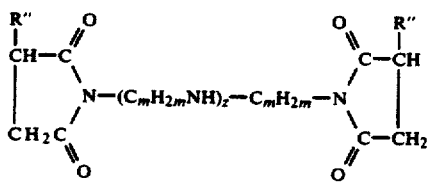

where z is an integer of from 1 to 10, m is an integer of from 2 to 12 and R" is an alkenyl group containing from 8 to about 10,000 carbon atoms.

12. The composition of claim 8 wherein said polyalkylene amine comprises tetraethylene pentamine.

13. The composition of claim 8 wherein said succinimide is the reaction product of about one molar equivalent of polyisobutenyl succinic anhydride containing from 8 to 10,000 carbon atoms and about one-half molar equivalent of tetraethylene pentamine; said triazole and diisocyanate reaction product comprise the reaction product of about equimolar equivalents of tolylenyl-triazole and tolylene diisocyanate.

14. A method for the production of liquid additive, comprising;
(a) reacting a diisocyanate compound with a 1,2,3-triazole whereby an addition reaction product is produced comprising said triazole containing a monoisocyanato group;
(b) reacting step (a) reaction product with the succinimide reaction product from the reaction of an alkyl or alkenyl succinic acid and a polyalkylene amine;
(c) recovering the reaction product from step (b) to provide said additive.

15. The method of claim 14 wherein the ratio of said triazole to diisocyanate to said succinimide is between 1:1:1 and 10:10:1.

16. The method of claim 14 wherein said diisocyanate comprises tolylene diisocyanate.

17. The method of claim 14 wherein said alkyl or alkenyl succinic acid, or derivative thereof, comprises polyisobutenyl succinic anhydride and said polyalkylene amine comprises tetraethylene pentamine.

18. A liquid lubricant composition comprising a major portion of an organic fluid lubricant medium and a minor portion of an additive in an amount sufficient to provide detergent, anti-oxidant or antiwear properties thereto, said additive comprising the composition according to claim 1 or 8.

19. A liquid composition comprising a major portion of an organic fluid or fuel medium and a minor portion of an additive in an amount sufficient to provide detergent, anti-oxidant or antiwear properties thereto, said additive prepared according to the method of claim 14.

20. The composition according to claim 18 wherein said lubricant comprises mineral oil or synthetic lubricant.

21. A method for improving the oxidative stability of mineral oil or synthetic lubricant, comprising; adding to said lubricant an amount of the composition according to claim 8 sufficient to provide a lubricant mixture with enhanced stability toward catalytic oxidative degradation.

22. The method of claim 21 wherein said composition is added to said lubricant in an amount between 0.1% and 10% by weight.

23. A fuel composition comprising a major portion of a fuel medium and a minor portion of an additive in an amount sufficient to provide detergent or dispersant properties thereto, said additive comprising the composition according to claim 8.

24. A fuel composition comprising a major portion of a fuel medium and a minor portion of an additive in an amount sufficient to provide detergent or dispersant properties thereto,, said additive prepared according to the method of claim 14.

* * * * *

UNITED STATES PATENT AND TRADEMARK OFFICE
CERTIFICATE OF CORRECTION

PATENT NO. : 4,994,197
DATED : February 19, 1991
INVENTOR(S) : D. A. Blain et al It is certified that error appears in the above-identified patent and that said Letters Patent is hereby corrected as shown below:

| | |
|---|---|
| Col. 8, line 45, Claim 1 | insert --,-- after "integers" |
| Col. 9, line 8, Claim 8 | delete [lubricant] |
| Col. 9, line 14, Claim 8 | delete [, or derivative thereof] |
| Col. 9, line 48, Claim 11 | delete [10] and insert --9-- |
| Col. 9, line 52, Claim 12 | delete [polyalkylene] insert --polyalkylenepoly-- |
| Col. 10, line 21, Claim 18 | delete [, or derivative thereof] |
| Col. 10, line 2, Claim 22 | insert --medium-- before "comprises" |

Signed and Sealed this

Twenty-first Day of July, 1992

*Attest:*

DOUGLAS B. COMER

*Attesting Officer*  *Acting Commissioner of Patents and Trademarks*